US008802669B2

(12) United States Patent
Li et al.

(10) Patent No.: US 8,802,669 B2
(45) Date of Patent: Aug. 12, 2014

(54) DIHYDROPYRIMIDINE COMPOUNDS AND PREPARATION METHODS, PHARMACEUTICAL COMPOSITIONS AND USES THEREOF

(75) Inventors: Song Li, Beijing (CN); Xiaoqian Xu, Beijing (CN); Guoming Zhao, Beijing (CN); Lili Wang, Beijing (CN); Hua Guan, Beijing (CN); Junhai Xiao, Beijing (CN); Wu Zhong, Beijing (CN); Zhibing Zheng, Beijing (CN); Yunde Xie, Beijing (CN); Xingzhou Li, Beijing (CN); Xiaokui Wang, Beijing (CN); Xinbo Zhou, Beijing (CN); Hongying Liu, Beijing (CN)

(73) Assignee: Institute of Pharmacology and Toxicology Academy of Military Medical Sciences, P.L.A. China, Beijing (CN)

( * ) Notice: Subject to any disclaimer, the term of this patent is extended or adjusted under 35 U.S.C. 154(b) by 285 days.

(21) Appl. No.: 13/380,270

(22) PCT Filed: May 27, 2010

(86) PCT No.: PCT/CN2010/000757
§ 371 (c)(1),
(2), (4) Date: Feb. 23, 2012

(87) PCT Pub. No.: WO2010/148631
PCT Pub. Date: Dec. 29, 2010

(65) Prior Publication Data
US 2012/0149695 A1 Jun. 14, 2012

(30) Foreign Application Priority Data

Jun. 25, 2009 (CN) .......................... 2009 1 0148630

(51) Int. Cl.
*C07D 239/20* (2006.01)
*C07D 401/06* (2006.01)
*C07D 401/14* (2006.01)
*A61K 31/505* (2006.01)
*A61K 31/506* (2006.01)
*C07D 211/14* (2006.01)
*A61K 31/4025* (2006.01)
*A61K 31/4453* (2006.01)

(52) U.S. Cl.
CPC .......... *C07D 239/20* (2013.01); *C07D 211/14* (2013.01); *A61K 31/4025* (2013.01); *A61K 31/4453* (2013.01); *A61K 31/505* (2013.01); *A61K 31/506* (2013.01)
USPC ................. 514/227.5; 514/235.8; 514/252.14; 514/256; 544/60; 544/122; 544/295; 544/335

(58) Field of Classification Search
CPC ............... C07D 239/20; C07D 211/14; A61K 31/4025; A61K 31/4453; A61K 31/505; A61K 31/506
USPC ................. 544/60, 122, 295, 335; 514/227.5, 514/235.8, 252.14, 256
See application file for complete search history.

(56) References Cited

U.S. PATENT DOCUMENTS

| 2010/0004268 A1 | 1/2010 | Li et al. |
| 2010/0087448 A1 | 4/2010 | Li et al. |
| 2010/0240655 A1 | 9/2010 | Siegfried et al. |

FOREIGN PATENT DOCUMENTS

| CN | 101575318 A | 11/2009 |
| EP | 2039686 A1 | 3/2009 |
| EP | 2048141 A1 | 4/2009 |
| WO | 2001068639 A1 | 9/2001 |
| WO | 2001068640 A1 | 9/2001 |
| WO | 2001068641 A1 | 9/2001 |
| WO | 2008154820 A1 | 12/2008 |

OTHER PUBLICATIONS

Razonable et al., PubMed Abstract (Herpes 10(3):60-5), Dec. 2003.*
Douglar, Jr. Introduction to Viral Diseases, Cecil Textbook of Medicine, 20th Edition, vol. 2, pp. 1739-1747, 1996.*
Golf, PubMed Abstract (J Gene Med. 3(6):517-28) Nov.-Dec. 2001.*
Bosseray et al., PubMed Abstract (Pathol. Biol. 50(8):483-92), Oct. 2002.*
Deres et al., "Inhibition of Hepatitis B Virus Replication by Drug-Induced Depletion of Nucleocapsids," Science, vol. 299, No. 5608, Feb. 7, 2003, pp. 893-896.
Weber et al., "Inhibition of human hepatitis B virus (HBV) by a novel non-nucleosidic compound in a transgenic mouse model," Antiviral Research, vol. 54, No. 2, Jan. 1, 2002, pp. 69-78.
Supplementary European Search Report for EP Application No. 10 79 1138, dated Oct. 4, 2012.
International Search Report for PCT/CN2010/000757 of Aug. 26, 2010.

* cited by examiner

*Primary Examiner* — Deepak Rao
(74) *Attorney, Agent, or Firm* — Banner & Witcoff, Ltd.

(57) ABSTRACT

Disclosed are dihydropyrimidine compounds and preparation methods, pharmaceutical compositions and uses thereof. Specifically, the compounds described herein in general formula (I), or their isomers, pharmaceutically acceptable salts or hydrates are provided, wherein each variable has the meaning as defined in the description. Also provided are a process for preparing the compounds of the general formula (I), the use of the compounds, an isomer thereof, a pharmaceutically acceptable salt thereof or a hydrate thereof as a medicament, in particular as a medicament for the treatment and/or prevention of Hepatitis B.

7 Claims, No Drawings

DIHYDROPYRIMIDINE COMPOUNDS AND PREPARATION METHODS, PHARMACEUTICAL COMPOSITIONS AND USES THEREOF

CROSS REFERENCE TO RELATED APPLICATIONS

This is a U.S. National Phase Application under 35 U.S.C. §371 of International Application No. PCT/CN2010/000757 filed May 27, 2010, which claims priority to Chinese Application No. 200910148630.2, filed Jun. 25, 2009, the entire contents of which are incorporated herein by reference.

TECHNICAL FIELD

The present invention relates to a novel dihydropyrimidine compound of general formula (I) and a process for preparing the compound, to a pharmaceutical composition comprising the compound, and to the use of the compound, or an isomer, pharmaceutically acceptable salt or hydrate thereof as a medicament such as an antiviral agent, in particular as a medicament for the treatment and/or prevention of Hepatitis B.

BACKGROUND ART

Chronic Hepatitis B is an infectious disease prevalent throughout the world, which is caused by hepatitis B virus (HBV) and is closely associated with the occurrence of hepatocirrhosis and liver cancer. China is a high prevalence area of Hepatitis B. The results of seropidemiological survey of viral hepatitis in China from 1992 to 1995 showed that the persons carrying the viral hepatitis B surface antigen (HBsAg) in China accounted for 9.7% of the population, and it was estimated that there are $1.3 \times 10^8$ HBV carriers. The study on the epidemic status of viral hepatitis in China showed that the annual reported incidence rate of hepatitis B increased from 21.9/100,000 in 1990 to 53.3/100,000 in 2003, which exhibited an obvious ascending trendency (see: Wang Xiaojun, Zhang Rongzhen and Hu Yuansheng et al, Disease Surveillance, 2004, 19(8): 290-292). Chronic Hepatitis B not only seriously affects the health of human body but also imposes heavy economic burden on family and society. Chronic Hepatitis B has become one of the important public health problems in China.

Drugs for the treatment of Chronic Hepatitis B usually belong to two main classes, i.e. immunomodulators and nucleoside DNA polymerase inhibitors (Loomba R., Liang T. J., Antivir. Ther., 2006, 11(1):1-15), in which the former includes interferon-α2b (IFN-α2b, Intron A®), while the latter includes Lamivudine (EPivir-HBV®), Adefovir Dipivoxil (Hepsera®) and Entecavir (Baracluda®). Comparatively speaking, there are quite few of drugs available for the clinical treatment of Hepatitis B. Therefore, it is of great significance to carry out continuous research and development of novel and safe antiviral drugs, in particular drugs having a new mechanism of action.

Deres et al reported the dihydropyrimidine compounds substituted with a heteroaryl cyclic group, with Bay41-4109 and Bay36-5493 as representatives, which compounds can inhibit HBV replication by obstructing the formation of normal nucleocapsids. The clinical data showed that Bay41-4109 has excellent drug metabolism parameters (Deres K., Schroder C. H., Paessens A., et al, Science, 2003, 299 (5608): 893-896). The study on the action mechanism of the compounds showed that the inclination between dimers for forming a nucleocapsid is changed due to the interaction between HAP and 113-114 amino residues of a core protein, so that a unstable and expanded nucleocapsid is formed to accelerate the degradation of the core protein (Hacker H. J., Deres K., Mildenberger M., et al., Biochem. Pharmacol., 2003, 66(12): 2273-2279).

At present, there is a need to develop a novel compound that is effectively useful as an antiviral agent, in particular, as a medicament for the treatment and/or prevention of Hepatitis B.

Contents of the Invention

It has been discovered by the inventors that a class of new dihydropyrimidine compounds of general formula (I) provided by the present invention have an effective antiviral effect, in particular against hepatitis B virus, and the present invention is completed based on this discovery.

SUMMARY OF THE INVENTION

The first aspect of the present invention is to provide a compound of general formula (I), or an isomer, pharmaceutically acceptable salt or hydrate thereof,

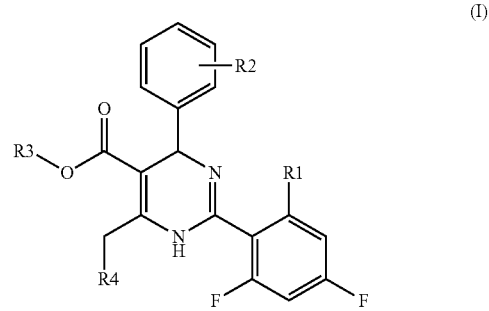

wherein:

R1 represents a halogen, a nitrogen-containing $(C_4-C_{14})$-heterocyclic group, a $(C_1-C_6)$-alkylamino or a $(C_1-C_6)$-alkoxy, in which the nitrogen-containing heterocyclic group and alkyl moiety are optionally substituted by hydroxyl, a $(C_1-C_6)$-alkoxy, a $(C_1-C_6)$-alkoxycarbonyl, an aryl, a substituted aryl or a $(C_1-C_6)$-alkyl;

R2, for one or more occurrences, each represents a substituent selected from a halogen, nitro, hydroxyl, sulphonyl, a straight or branched $(C_1-C_6)$-alkyl, a $(C_1-C_6)$-alkoxyl, a $(C_1-C_6)$-alkoxycarbonyl, amino, a mono- or di-substituted amino, or an amido;

R3 represents a $(C_1-C_6)$-alkyl; and

R4 represents a halogen, a nitrogen-containing $(C_4-C_8)$-heterocyclic group, a $(C_1-C_6)$-alkylamino, a $(C_1-C_6)$-alkoxy, or a bi$(C_1-C_6)$-alkylamino, in which the nitrogen-containing heterocyclic group and alkyl moiety are optionally substituted by hydroxyl, a $(C_1-C_6)$-alkoxy, a $(C_1-C_6)$-alkoxycarbonyl, an aryl, a substituted aryl, oxo or a $(C_1-C_6)$-alkyl.

The first aspect of the present invention is to provide a compound of general formula (Ia), or an isomer, pharmaceutically acceptable salt or hydrate thereof,

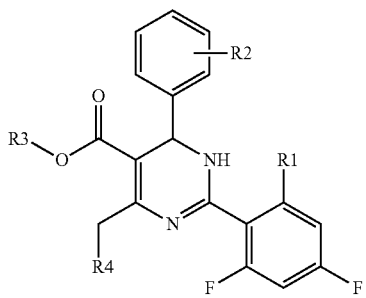

(Ia)

wherein:

R1 represents a halogen, a nitrogen-containing ($C_4$-$C_{14}$)-heterocyclic group, a ($C_1$-$C_6$)-alkylamino or a ($C_1$-$C_6$)-alkoxy, in which the nitrogen-containing heterocyclic group and alkyl moiety are optionally substituted by hydroxyl, a ($C_1$-$C_6$)-alkoxy, a ($C_1$-$C_6$)-alkoxycarbonyl, an aryl, a substituted aryl or a ($C_1$-$C_6$)-alkyl;

R2, for one or more occurrences, each represents a substituent selected from a halogen, nitro, hydroxyl, sulphonyl, a straight or branched ($C_1$-$C_6$)-alkyl, a ($C_1$-$C_6$)-alkoxyl, a ($C_1$-$C_6$)-alkoxycarbonyl, amino, a mono- or di-substituted amino, or an amido;

R3 represents a ($C_1$-$C_6$)-alkyl; and

R4 represents a halogen, a nitrogen-containing ($C_4$-$C_8$)-heterocyclic group, a ($C_1$-$C_6$)-alkylamino, a ($C_1$-$C_6$)-alkoxy, or a bi($C_1$-$C_6$)-alkylamino, in which the nitrogen-containing heterocyclic group and alkyl moiety are optionally substituted by hydroxyl, a ($C_1$-$C_6$)-alkoxy, a ($C_1$-$C_6$)-alkoxycarbonyl, an aryl, a substituted aryl, oxo or a ($C_1$-$C_6$)-alkyl.

The compounds of general formula (I) or (Ia), or an isomer, pharmaceutically acceptable salt or hydrate thereof, according to the first aspect of the present invention, wherein:

R1 represents a halogen, a nitrogen-containing ($C_4$-$C_8$)-heterocyclic group, a ($C_1$-$C_4$)-alkylamino or a ($C_1$-$C_4$)-alkoxy, in which the nitrogen-containing heterocyclic group and alkyl moiety are optionally substituted by hydroxyl, a ($C_1$-$C_4$)-alkoxy, a ($C_1$-$C_4$)-alkoxycarbonyl, an aryl, a substituted aryl or a ($C_1$-$C_4$)-alkyl;

R2 represents a substituent selected from a halogen, nitro, hydroxyl, sulphonyl straight or branched ($C_1$-$C_4$)-alkyl, a ($C_1$-$C_4$)-alkoxyl, a ($C_1$-$C_4$)-alkoxycarbonyl, amino, a mono- or di-substituted amino, or an amido;

R3 represents a ($C_1$-$C_4$)-alkyl; and

R4 represents a halogen, a nitrogen-containing ($C_4$-$C_8$)-heterocyclic group, a ($C_1$-$C_4$)-alkylamino, a ($C_1$-$C_4$)-alkoxy, or a bi($C_1$-$C_4$)-alkylamino, in which the nitrogen-containing heterocyclic group and alkyl moiety are optionally substituted by hydroxyl, a ($C_1$-$C_4$)-alkoxy, a ($C_1$-$C_4$)-alkoxycarbonyl, an aryl, a substituted aryl, oxo or a ($C_1$-$C_4$)-alkyl.

In one embodiment, provided are the compounds of general formula (I) or (Ia), or an isomer, pharmaceutically acceptable salt or hydrate thereof, according to the first aspect of the present invention, wherein:

R1 represents fluoro, tetrahydropyrrolyl, hexahydropyridyl, 4-methylpiperidyl, morpholinyl, thiomorpholinyl, 4-methyl piperazinyl, 4-ethylpiperazinyl, 4-propylpiperazinyl, diethanolamino, 4-ethoxylacylpiperazinyl, 3-oxopiperazinyl, methoxy or ethoxy;

R2 represents fluoro, chloro, bromo, iodo, hydroxyl, nitro, methyl, methoxy, amino or acetylamino;

R3 represents methyl, ethyl or propyl; and

R4 represents chloro, tetrahydropyrrolyl, hexahydropyridyl, 4-methylpiperidyl, morpholinyl, thiomorpholinyl, 4-methyl piperazinyl, 4-ethylpiperazinyl, 4-propylpiperazinyl, diethanolamino, 4-ethoxylacylpiperazinyl or 3-oxopiperazinyl.

In one embodiment, provided are the compounds of general formula (I) or (Ia), or an isomer, pharmaceutically acceptable salt or hydrate thereof, according to the first aspect of the present invention, which are selected from:

(1) ethyl 2-(2,4,6-trifluorophenyl)-4-(2-chloro-4-fluorophenyl)-6-(chloromethyl)-1,4-dihydropyrimidine-5-carboxylate;

(2) ethyl 2-(2,4,6-trifluorophenyl)-4-(2-chloro-4-fluorophenyl)-6-(tetrahydropyrrol-1-ylmethyl)-1,4-dihydropyrimidine-5-carboxylate;

(3) ethyl 2-(2,4,6-trifluorophenyl)-4-(2-chloro-4-fluorophenyl)-6-(hexahydropyridin-1-ylmethyl)-1,4-dihydropyrimidine-5-carboxylate;

(4) ethyl 2-(2,4,6-trifluorophenyl)-4-(2-chloro-4-fluorophenyl)-6-(4-methylpiperidin-1-ylmethyl)-1,4-dihydropyrimidine-5-carboxylate;

(5) ethyl 2-(2,4,6-trifluorophenyl)-4-(2-chloro-4-fluorophenyl)-6-(morpholin-1-ylmethyl)-1,4-dihydropyrimidine-5-carboxylate;

(6) ethyl 2-(2,4,6-trifluorophenyl)-4-(2-chloro-4-fluorophenyl)-6-(thiomorpholin-1-ylmethyl)-1,4-dihydropyrimidine-5-carboxylate;

(7) ethyl 2-(2,4,6-trifluorophenyl)-4-(2-chloro-4-fluorophenyl)-6-(4-methylpiperazin-1-ylmethyl)-1,4-dihydropyrimidine-5-carboxylate;

(8) ethyl 2-(2,4,6-trifluorophenyl)-4-(2-chloro-4-fluorophenyl)-6-(4-ethylpiperazin-1-ylmethyl)-1,4-dihydropyrimidine-5-carboxylate;

(9) ethyl 2-(2,4,6-trifluorophenyl)-4-(2-chloro-4-fluorophenyl)-6-(4-propylpiperazin-1-ylmethyl)-1,4-dihydropyrimidine-5-carboxylate;

(10) ethyl 2-[2,4-difluoro-6-(tetrahydropyrrol-1-yl)phenyl]-4-(2-chloro-4-fluorophenyl)-6-(tetrahydropyrrol-1-ylmethyl)-1,4-dihydropyrimidine-5-carboxylate;

(11) ethyl 2-[2,4-difluoro-6-(hexahydropyridin-1-yl)phenyl]-4-(2-chlor-4-fluorophenyl)-6-(hexahydropyridin-1-ylmethyl)-1,4-dihydropyrimidine-5-carboxylate;

(12) ethyl 2-[2,4-difluoro-6-(4-methylpiperidin-1-yl)phenyl]-4-(2-chloro-4-fluorophenyl)-6-(4-methylpiperidin-1-ylmethyl)-1,4-dihydropyrimidine-5-carboxylate;

(13) ethyl 2-[2,4-difluoro-6-(morpholin-1-yl)phenyl]-4-(2-chlor-4-fluorophenyl)-6-(morpholin-1-ylmethyl)-1,4-dihydropyrimidine-5-carboxylate;

(14) ethyl 2-[2,4-difluoro-6-(4-methylpiperazin-1-yl)phenyl]-4-(2-chlor-4-fluorophenyl)-6-(4-methylpiperazin-1-ylmethyl)-1,4-dihydropyrimidine-5-carboxylate;

(15) ethyl 2-(2,4,6-trifluorophenyl)-4-(2-chloro-4-fluorophenyl)-6-diethanolaminomethyl-1,4-dihydropyrimidine-5-carboxylate;

(16) ethyl 2-(2,4,6-trifluorophenyl)-4-(2-chloro-4-fluorophenyl)-6-(4-ethoxylacylpiperazin-1-ylmethyl)-1,4-dihydropyrimidine-5-carboxylate;

(17) ethyl 2-(2,4,6-trifluorophenyl)-4-(2-chloro-4-fluorophenyl)-6-[(3-oxopiperazin-1-yl)methyl]-1,4-dihydropyrimidine-5-carboxylate; and

(18) ethyl 2-(2,4,6-trifluorophenyl)-4-(2-chloro-4-fluorophenyl)-6-(morpholin-1-ylmethyl)-1,4-dihydropyrimidine-5-carboxylate hydrochloride.

The second aspect of the present invention is to provides a process for preparing a compound of general formula (I) or (Ia) according to any one embodiment of the first aspect of the present invention, in particular the compound of general formula (I), which process comprises:

step A): reacting 2,4,6-trifluorobenzamidine or a salt thereof with a substituted benzaldehyde of the formula

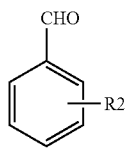

wherein R2 has the same meaning as defined for the compound of general formula (I) or (Ia) according to any one embodiment of the first aspect of the present invention, and a 4-chloroacetyl acetate of the formula

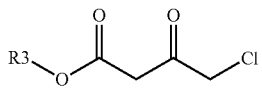

wherein R3 has the same meaning as defined for the compound of general formula (I) or (Ia) according to any one embodiment of the first aspect of the present invention, in a suitable inert solvent with or without addition of a base or an acid to provide a compound of the formula (II);

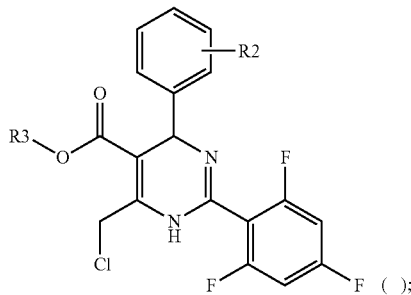

and,
wherein R2 and R3 each have the same meaning as defined for the compound of general formula (I) or (Ia) according to any one embodiment of the first aspect of the present invention, optionally step B): reacting the product of the step A), the compound of formula (II) with a compound of the formula R4H wherein R4 is as defined for the compound of general formula (I) or (Ia) according to any one embodiment of the first aspect of the present invention except for chloro, in a suitable inert solvent with addition of a base to obtain a compound of general formula (I).

The third aspect of the present invention is to provide a pharmaceutical composition comprising therapeutically and/or preventively effective amount of a compound of general formula (I) or (Ia) according to any one embodiment of the first aspect of the present invention, optionally pharmaceutically acceptable carriers, and optionally other pharmaceutically active compounds.

The fourth aspect of the present invention is to provide use of a compound of general formula (I) or (Ia) according to any one embodiment of the first aspect of the present invention in the manufacture of a medicament for treating and/or preventing acute or chronic viral diseases.

The fifth aspect of the present invention is to provide use of a compound of general formula (I) or (Ia) according to any one embodiment of the first aspect of the present invention in the manufacture of a medicament for treating and/or preventing acute or chronic infections caused by hepatitis B viruses.

The sixth aspect of the present invention is to provide a method of treating and/or preventing acute or chronic viral disease, comprising administering a subject in need thereof a therapeutically and/or preventively effective amount a compound of general formula (I) or (Ia) according to any one embodiment of the first aspect of the present invention.

The seventh aspect of the present invention to provide a method of treating and/or preventing acute or chronic infections caused by hepatitis B viruses, comprising administering a subject in need thereof a therapeutically and/or preventively effective amount a compound of general formula (I) or (Ia) according to any one embodiment of the first aspect of the present invention.

DETAILED DESCRIPTIONS OF THE INVENTION

As for all references cited in the present invention, their contents are incorporated herein by reference, and if the meanings expressed in these documents are not in consistence with the present invention, the expressions of the present invention should be used. In addition, the terms and phrases used in the present invention have the general meanings well known by those skilled in the art, nevertheless, these terms and phrases may be further explained and demonstrated in detail at here, and if the meanings of the mentioned terms and phrases are not in consistence with those well known in the art, the meanings recited in the present application should be used.

In the specification of the present application, the term "halogen" or "halogenated" refers to fluorine, chlorine, bromide and iodine.

In the specification of the present application, the term "a nitrogen-containing $(C_4-C_{14})$-heterocyclic ring" refers to a heterocyclic system having specified carbon atom number and further comprising heteroatom(s) e.g. O or S in addition to N, which may comprise a condensed bicyclic or tricyclic rings.

In the specification of the present application, the term "$(C_1-C_6)$-alkylamino" refers to a straight or branched group having 1-6 carbon atoms, including but not being limited to methylamino, ethylamino, n-propylamino, iso-propylamino, n-butylamino, sec-butylamino, iso-butylamin, tert-butylamino, or the like. In the specification of the present application, the term "$(C_1-C_6)$-alkoxy" refers to a straight or branched group having 1-6 carbon atoms, including but not being limited to methoxy, ethoxy, n-propoxy, iso-propoxy, n-butoxy, sec-butoxy, iso-butoxy, tert-butoxy, or the like.

In the specification of the present application, the term "$(C_1-C_6)$-alkoxycarbonyl" refers to a straight or branched alkoxycarbonyl having 1-6 carbon atoms, including but not being limited to methoxycarbonyl, ethoxycarbonyl, n-propoxycarbonyl, iso-propoxycarbonyl, n-butoxycarbonyl, sec-butoxycarbonyl, iso-butoxycarbonyl, tert-butoxycarbonyl, or the like.

In the specification of the present application, the term "$(C_1-C_6)$-alkyl" refers to a straight or branched group having 1-6 carbon atoms, including but not being limited to methyl, ethyl, n-propyl, iso-propyl, n-butyl, sec-butyl, iso-butyl, tert-butyl, or the like.

In the specification of the present application, the term "isomer" may include various types of isomers, including but not being limited to any tautomers, optical isomers, enantiomes, isomerides, or the like.

In the specification of the present application, the term "oxo", for example, the "oxo" in a substituent of R4 as a nitrogen-containing heteocyclic group means that a ring atom in the nitrogen-containing heteocyclic group, such as a ring carbon atom, is substituted by "oxo-yl" such that the ring carbon atom forms carbonyl. For instance, when R4 is

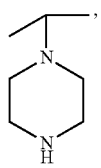, a ring carbon atom thereof may be substituted by "oxo-yl" to form

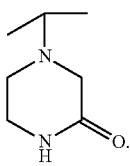.

The compounds of the present invention may include the compounds of general formula (I) and isomers (Ia) thereof and their mixtures. The compounds of general formula (I) and isomers (Ia) exist in a tautomeric equilibrium in a solution:

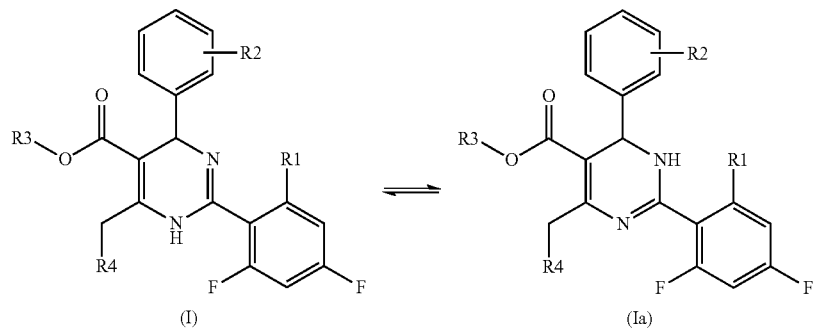

The compounds according to the present invention may exist in the form of optical isomers which are present as enantiomers or diastereomers. The present invention relates to a mixture of the enantiomers or diastereomers.

The compounds according to the present invention may also be present as salts, and the preferred are the pharmaceutically acceptable salts. The pharmaceutically acceptable salts include but are not limited to the salts of the compounds according to the present invention with inorganic acids such as hydrochloric acid, sulfuric acid, phosphoric acid, hydrobromic acid or nitric acid, or with organic acids such as maleic acid, fumaric acid, malic acid, furmaric acid, succinic acid, tartaric acid, citric acid, acetic acid, lactic acid, benzoic acid, methanesulphonic acid, ethanesulphonic acid, phenylsulphonic acid, para-toluenesulphomic acid, palmitic acid, or the like.

The pharmaceutically acceptable salts can also include but are not limited to the metal salts of the compounds according to the present invention, such as sodium, potassium, magnesium or calcium salts, and the ammonium salts formed with organic amines such as ethylamine, diethylamine, triethylamine, diethanolamine, triethanolamine, dicyclohexylamine, dimethylaminoethanol, arginine, lysine, ethylenediamine, 2-phenylethylamine, or the like.

Some compounds according to the present invention may be crystallized or recrystallized with water or various organic solvents. Under this circumstance, it is possible to form various solvates. The present invention includes stoechiometric solvates, hydrates and compounds containing variable water formed during the preparation by lyophylization.

Although the compounds of the formulae (I) and (Ia) are explicitly defined in the Summary of the Invention part of the specification, they are still further described herein. Specifically, preference is given to compounds of general formula (I) or isomers thereof, and salts or hydrates thereof, in which:

R1 halogen, a nitrogen-containing ($C_4$-$C_8$)-heterocyclic group, a ($C_1$-$C_4$)-alkylamino or a ($C_1$-$C_4$)-alkoxy, in which the nitrogen-containing heterocyclic group and alkyl moiety are optionally substituted by hydroxyl, a ($C_1$-$C_4$)-alkoxy, a ($C_1$-$C_4$)-alkoxycarbonyl, an aryl, a substituted aryl or a ($C_1$-$C_4$)-alkyl;

R2 represents a substituent selected from a halogen, nitro, hydroxyl, sulphonyl, a straight or branched ($C_1$-$C_4$)-alkyl, a ($C_1$-$C_4$)-alkoxyl, a ($C_1$-$C_4$)-alkoxycarbonyl, amino, a mono- or di-substituted amino, or an amido;

R3 represents a ($C_1$-$C_4$)-alkyl; and

R4 represents a halogen, a nitrogen-containing ($C_4$-$C_8$)-heterocyclic group, a ($C_1$-$C_4$)-alkylamino or a ($C_1$-$C_4$)-alkoxy, in which the nitrogen-containing heterocyclic group and alkyl moiety are optionally substituted by hydroxyl, a ($C_1$-$C_4$)-alkoxy, a ($C_1$-$C_4$)-alkoxycarbonyl, an aryl, a substituted aryl, oxo or a ($C_1$-$C_4$)-alkyl.

In addition, the particularly preferred compounds of the invention are the compounds of general formula (I) or isomers thereof, and salts or hydrates thereof, in which:

R1 represents fluoro, tetrahydropyrrolyl, hexahydropyridyl, 4-methylpiperidyl, morpholinyl, thiomorpholinyl, 4-methyl piperazinyl, 4-ethylpiperazinyl, 4-propylpiperazinyl, diethanolamino, 4-ethoxylacylpiperazinyl, 3-oxopiperazinyl, methoxy or ethoxy;

R2 represents fluoro, chloro, bromo, iodo, hydroxyl, nitro, methyl, methoxy, amino or acetylamino;

R3 represents methyl, ethyl or propyl; and

R4 represents chloro, tetrahydropyrrolyl, hexahydropyridy, 4-methylpiperidyl, morpholinyl, thiomorpholinyl, 4-methyl piperazinyl, 4-ethylpiperazinyl, 4-propylpiperazinyl, diethanolamino, 4-ethoxylacylpiperazinyl or 3-oxopiperazinyl.

The particularly preferred compounds of general formula (I), or isomers thereof, or salts, or hydrates thereof, according to the present invention, are those embodied in the examples of the present application.

The compounds of general formula (I) of the present invention can be prepared by the following process comprising:

A) reacting 2,4,6-trifluorobenzamidine or a salt thereof with a substituted benzaldehyde of the following formula

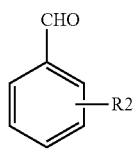

wherein R2 has the same meaning as defined above, and a 4-chloroacetyl acetate of the following formula

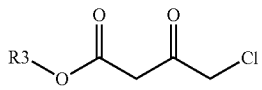

wherein R3 has the same meaning as defined above, in a suitable inert solvent (such as ethanol, in particular e.g. anhydrous ethanol) with or without addition of a base or an acid (such as hydrochloric acid) to provide an exemplary compound of the formula (II)

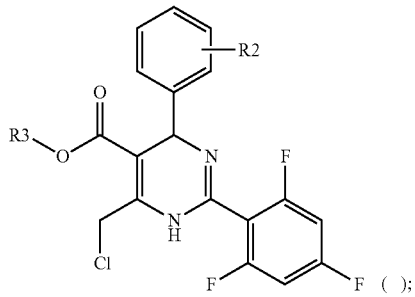

and wherein R2 and R3 each have the same meaning as defined above, optionally B): reacting the product of the step A), the compound of formula (II) with a compound of formula R4H wherein R4 is defined as above except for chloro, to obtain a compound of general formula (I) in a suitable inert solvent with addition of a base.

Processes for the preparation of the compounds of the present invention are illustrated in the following schemes as examples:

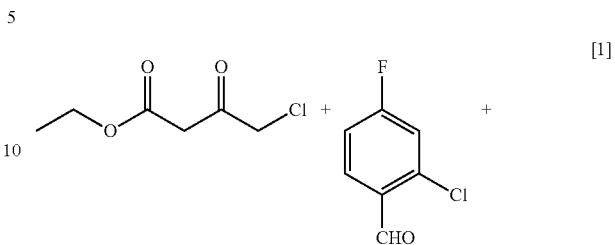

[1]

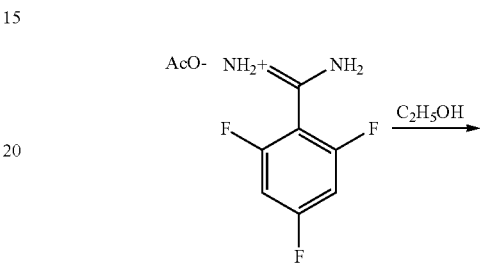

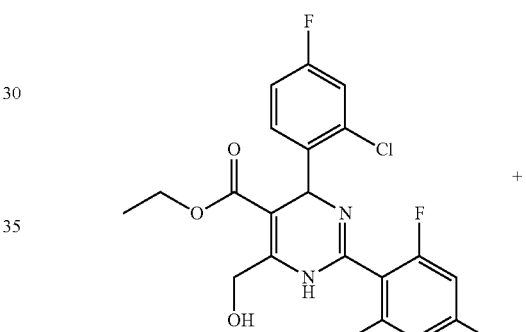

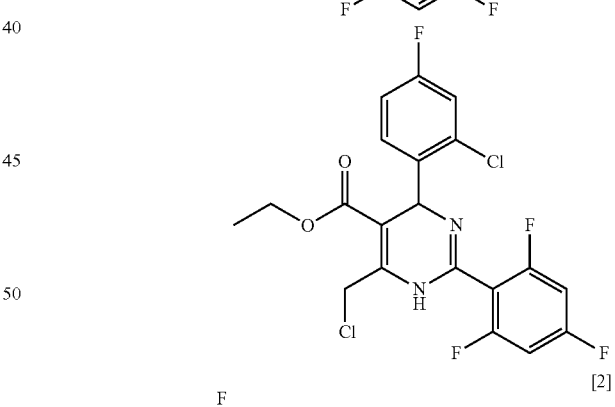

[2]

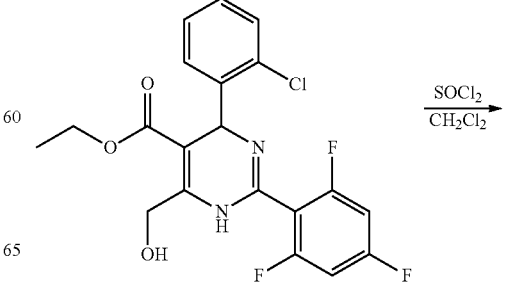

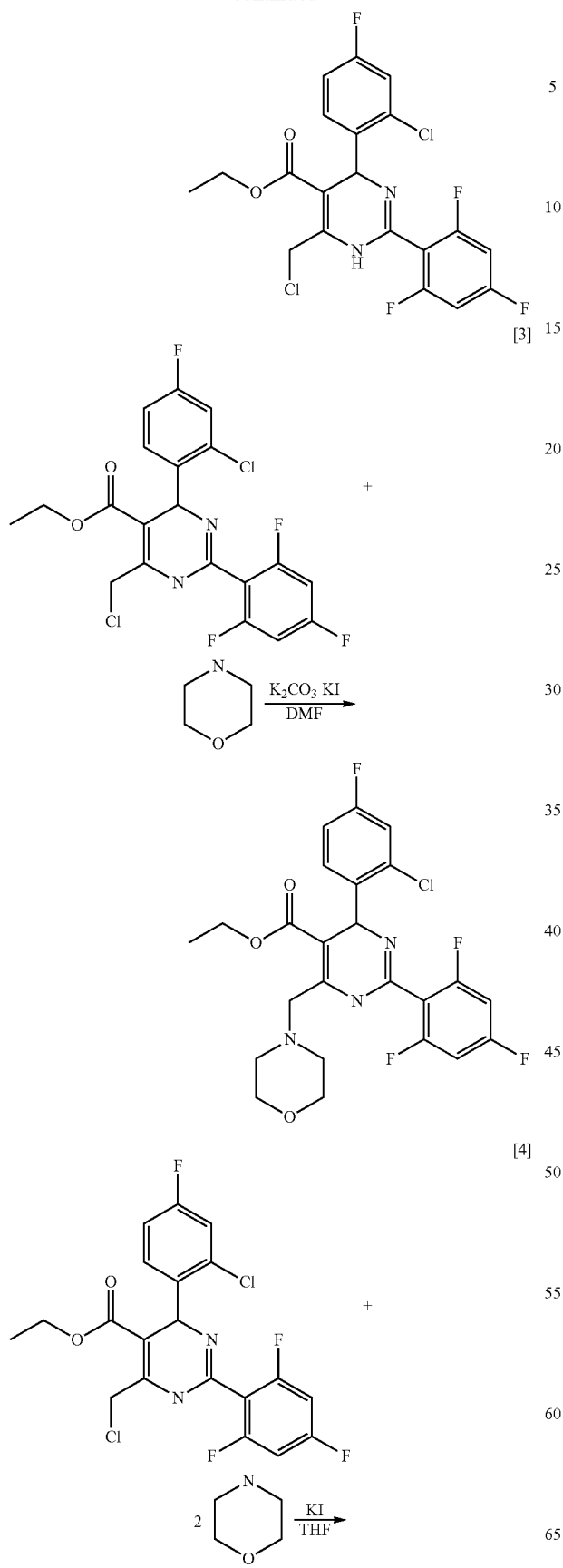

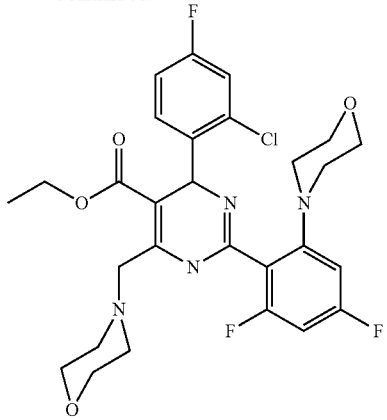

As far as the aforesaid reaction schemes are concerned, solvents which are suitable for reaction scheme [1] are any inert organic solvents. Preferably, the solvent includes alcohols, such as ethanol, methanol, isopropanol, ethers such as dioxane, ethyl ether, tetrahydrofuran, glycol monomethyl ether, glycol dimethyl ether or glacial acetic acid, dimethyl formamide, dimethyl sulphoxide, acetonitrile, pyridine and hexamethyl phosphoramide.

Solvents which are suitable for reaction scheme [2] are any inert organic solvents. Preferably, the solvent includes halogenated hydrocarbons such as dichloromethane and trichloromethane, alcohols such as ethanol, methanol, iso-propanol, and thionyl chloride.

Solvents which are suitable for reaction schemes [3] and [4] are any aprotic organic solvents. Preferably, the solvent includes tetrahydrofuran, N—N-dimethylformamide, acetonitrile, acetone, and dichloromethane.

The reaction temperature of the reaction schemes [1] and [2] can be varied within a relatively wide range. In general, the reaction is carried out between 20 and 150° C., but preferably at the boiling point of each of the solvents.

The reaction temperature of the reaction schemes [3] and [4] can be varied within a relatively wide range. In general, the reaction is carried out between 0 and 150° C., but preferably at the room temperature.

The reaction can be carried out either at the atmospheric pressure, or at an elevated pressure. In general, the reaction is carried out at the atmospheric pressure.

The reaction scheme [1] can be carried out with or without addition of base or acid. The organic acids are such as, for example, formic acid, glacial acetic acid, methanesulphonic acid and para-toluenesulphonic acid, and the inorganic acids are such as, for example, hydrochloric acid, sulfuric acid, phosphoric acid and nitric acid. However, it is has been found that the reaction according to the present invention is preferably carried out in the presence of an inorganic acid such as hydrochloride acid.

Bases which are suitable for the reaction schemes [3] and [4] preferably include organic bases such as triethylamine, methyldiethylamine, pyridine, hexahydropyridine and morpholine, and inorganic bases such as sodium carbonate, potassium carbonate, sodium hydrogen carbonate, sodium acetate, sodium hydroxide and potassium hydroxide. However, it is has been found that the reactions according to the present invention are preferably carried out in the presence of a relatively weak base such as potassium carbonate.

The 2,4,6-trifluorobenzamidine acetate used as a starting material can be prepared from the corresponding cyano compounds by the methods known from the literatures (cf. Diana, G. D., Yarinsky, A., Zalay, E. S., et al, J. Med. Chem., 1969, 12(9): 791-793; Boere, R. J., Oakley, R. T., Read, R. V., J. Organometal. Chem., 1987, 331: 161-167; Judikins, B. D., Allen, D. g., Cook, T. A., Synth. Commun., 1996, 26(23): 4351-4367).

The 2-chloro-4-fluorobenaldehyde as a starting material is known or can be prepared by methods known from the literatures (cf. T. D. Harris and G. P. Roth, J. Org. Chem., 1979, 44: 1446; DE 2165260, July 1972; DE2401665, July 1974; Mijano et. Al, CA 1963, 59, 13929c; E. Adler, H. D. Becker, Chem. Scand., 1961, 15, 849; E. P. Papadopoulos, M. Mardin, Ch. Issidoridis, J. Org. Chem. Sco., 1956, 78, 2543).

The compounds of general formula (I) according to the present invention can be individually synthesized by conventional methods, or synthesized in the form of libraries (each library comprises at least two, or from 5 to 1000, more preferably from 10 to 100, of compounds) by mix-split or parallel synthesis process in combinatorial chemistry. The compounds according to the present invention can be synthesized in a liquid phase or solid phase synthesis.

More detailed information on the preparation of the compounds of general formula (I) are provided in the following examples.

The antiviral activity of the compounds according to the present invention was tested following the methods described by Sells et al. (M. A. Sells, M. L. Chen, g. Acs, Proc. Natl. Acad. Sci., 1987, 84, 1005-1009) and Korba et al., (B. E. Korba, J. L. Gerin, Antiviral Research, 1992, 19. 55-70).

The antiviral tests were carried out in 96-well microtitre plates. Only growth medium and HepG2.2.15 cells were added to the first vertical row of the plate, which row severed as a blank control.

Stock solutions of the test compounds (50 mM) were initially dissolved in DMSO, and further dilutions were prepared in the growth medium of HepG2.2.15. The compounds according to the present invention, usually in a test concentration of 100 μg/ml (1st test concentration), were in each case pipetted into the second vertical test row of the microtitre plate and subsequently diluted by a factor of 2 each time, up to $2^{10}$-fold, using growth medium plus 2% of foetal calf serum (volume 25 μl).

225 μl of a HepG2.2.15 cell suspension ($5 \times 10^4$ cells/ml) in growth medium plus 2% foetal calf serum were then added to each well of the microtitre plate.

The test batch was incubated at 37° C., 5% $CO_2$ for 4 days. The supernatant was subsequently siphoned off and discarded, and 225 μl of freshly prepared growth medium were added to the wells. Once more, the compounds according to the present invention were added, in a volume 25 μl. The batches were incubated fro another 4 days.

Before the supernatants were harvested for determining the antiviral effect, the HePG2.2.15 cells were examined under the light microscope or by biochemical detection methods (for example Alamar Blue staining or Trypan Blue staining) for cytotoxic changes.

The supernatants were subsequently harvested and, by means of reduced pressure, siphoned onto 96-well dot blot chambers covered with a nylon membrane (in accordance with the specification provided by the manufacturer).

Determination of the Cytotoxicity

Substances-induced cytotoxic or cytostatic changes in the HepG2.2.15 cells were determined as changes in the cell morphology, for example under a light microscope. Such substance-induced changes of the HepG2.2.15 cells in comparison with untreated cells was apparent, for example, as cell lysis, vacuolization changed cell morphology. The pathological changes were observed by microscope after 8 days as index, a complete destroy being indicated as 4, 75% as 3, 50% as 2, 25% as 1, and no pathological change as 0. The average pathological change degree and inhibited percentages at various concentration were calculated, and a half-maximum toxic concentration ($TC_{50}$) and a maximum non-toxic concentration $TC_{50}$ were determined according to Reed & Muench methods.

$TC_{50}$ means the concentration at which 50% of the cells have a morphology which is similar to the corresponding cell control by the compounds according to the present invention.

Determination of the Antiviral Activity

After transfer of the supernatants onto the nylon membrane of the blot apparatus (see above), the supernatants of the HepG2.2.15 cells were denatured (1.5 M NaCl/0.5 N NaOH), neutralized (3 M NaI/0.5 M Tris HCl, pH 7.5) and washed (2×SSC). By incubation of the filters at 120° C. for 2-4 hours, the DNA was subsequently baked onto the membrane.

Hybridization of the DNA

The viral DNA of the treated HEpG2.2.15 cells on the nylon filter membrane was usually detected using non-radioactive digoxygenin-labelled hepatitis B-specific DNA probes which were in each case in accordance with the specifications of the manufacturer labelled with digoxygenin, purified and used for hybridization.

Briefly speaking, the prehybridization and hybridization were carried out in 5×SSC, 1×blocking reagent, 0.1% N-lauroylsacosine, 0.02% SDS and 100 μg of DNA from herring sperm. The prehybridization was carried out at 60° C. for 30 minutes and the specific hybridization was carried out using 20 to 40 ng/ml of the digoxygenated denatured HBV-specific DNA (14 hours, 60° C.). The fillers were subsequently washed, and then determination of HBV DNA by digoxygenin antibodies was carried out.

The digoxygenin-labelled DNA was detected immunologically in accordance with the specifications of the manufacturer.

Briefly speaking, the fillers were washed and prehybridized in a blocking agent (in accordance with the specifications of the manufacturer). They were subsequently hybridized for 30 minutes using an anti-DIG antibody linked to alkaline phosphatase. After a washing step, the substrate of alkaline phosphatase, CSPD, was added, incubated with the filters for 5 minutes, subsequently wrapped in plastic film and incubated at 37° C. for a further 15 minutes. The chemiluminescence of the Hepatitis B-specific DNA signals was visualized by exposition of the filters on an X-ray film (incubation, depending on the signal strength: 10 minutes to 2 hours). The half-maximum inhibitory concentration ($IC_{50}$) was determined.

The half-maximum inhibitory concentration ($IC_{50}$) means the concentration at which the hepatitis B-specific band was reduced by 50% in comparison with an untreated sample by the compound according to the present invention.

The compounds according to the present invention exhibited a relatively strong action against viruses. Such compounds have a surprisingly antiviral activity against hepatitis B (HBV) and are therefore suitable for treating virus-caused diseases, in particular acute and chronically persisting HBV virus infections. A chronic viral disease caused by HBV can lead to clinical pictures of various gravities. As is known, chronic hepatitis B virus infection frequently results in cirrhosis of the liver and/or hepatocellular carcinoma.

The Indications for which the compounds of the present invention may treat are:

The treatment of acute and chronic virus infections which may lead to an infectious hepatitis, for example, infections caused by hepatitis B viruses. Particular preference is given to the treatment of chronic hepatitis B infections and the treatment of acute hepatitis B virus infection.

The pharmaceutical composition comprising the compound of the present invention can be administered by any one of following routes: oral, spray inhalation, rectal, nasal cavity, vaginal, topical, parenteral, such as subcutaneous, intravenous, intramuscular, intraperitoneally, intrathecal, intraventricular, intrasternal or intracel injection or importation, or administered by means of an explanted reservoir, preferably oral administration, intramuscular injection, intraperitoneral or intravenous administration.

The compound according to the present invention or a pharmaceutical composition comprising the compound of the present invention can be administered in unit dose form. Administration dosage form can be a liquid or solid dosage form. The liquid dosage form can be true solutions, colloids, particulates, emulsions, suspensions. Other dosage forms include, e.g., tablets, capsules, drop pills, aerosols, pills, powders, solutions, suspensions, emulsions, particulates, suppositories, lyophilized powders, clathrates, embeddings, patches, embrocations, and so on.

The pharmaceutical composition of the present invention further comprises pharmaceutically acceptable carriers, herein the pharmaceutically acceptable carriers include but are not limited to: ion exchangers, alumina, aluminum stearate, lecithin, serum protein such as human serum protein, buffers such as phosphate, glycerol, sorbic acid, potassium sorbate, partial glycerolipid mixtures of saturated vegetable fatty acids, water, salts or electrolytes, such as potamine sulfate, disodium hydrogen phosphate, potassium hydrogen phosphate, sodium chloride, zinc salts, colloidal silica, magnesium, trisilicate, polyvinylpyrrolidone, cellulose materials, polyglycol, carboxylmethylcellulose sodium, polyacrylate, beeswax, lanolin, and so on. The content of carriers in the pharmaceutical composition can be 1% to 98% by weight, generally about 80% by weight. For convenience, topical anesthetic, preservative and buffer, etc. can be directly dissolved in the carriers.

Oral tablets and capsules can contain excipients, such as binders, e.g., syrup, gum Arabic, sorbitol, bassora gum, or polyvinyl pyrrolidone, fillers, e.g., lactose, sucrose, corn starch, calcium phosphate, sorbitol, animoacetic acid, lubricants, e.g., magnesium stearate, talc, polyglycol, silica, disintegrants, e.g., potato starch, or pharmaceutically acceptable wetting agents, such as sodium lauryl sulfate. The tablets can be coated by the methods known in the field of pharmaceutics.

Oral liquids can be prepared into suspensions of water and oil, solutions, emulsions, syrups or elixirs, and can also be prepared into dried products, which are supplied with water or other suitable vehicle before use. This liquid formulation can contain routine additives, such as a suspending agent, sorbitol, cellulose methyl ether, glucose syrup, gel, hydroxyethylcellulose, carboxylmethylcellulose, aluminum stearate gel, hydrogenated edible fats, emulsifiers, such as lecithin, Span-80, Arabic gum; or non-aqueous carriers (which may contain edible oils), such as almond oil, fats, such as glycerol, ethylene glycol, or ethanol; preservatives, such as methyl p-hydroxybenzoate or propyl p-hydroxybenzoate, sorbic acid. If required, flavoring agents or coloring agents can be added.

Suppositories can contain routine suppository, such as cocoa butter or other glycerides.

For parenteral administration, liquid dosage forms are usually formulated from a compound and a sterile carrier. The carrier is principally selected from water. According to the difference of the carrier selected and the concentration of pharmaceutical, the compound can be dissolved into the carrier and prepared into a suspension. When an injection solution is prepared, the compound is dissolved into water, then filtrated, disinfected and packed into seal bottle or ampoule.

When administered topically to the skin, the compounds according to the present invention can be prepared into a suitable form of ointment, lotion, or cream, in which the active ingredient is suspended or dissolved into one or more carriers. The carrier for use in ointment formulation includes but is not limited to mineral oil, liquid paraffin, white paraffin, propanediol, polyethylene oxide, polyoxytrimethylene, emulsifying wax and water; the carrier for use in lotion and cream includes but is not limited to mineral oil, sorbitan monostearate, Tween-60, cetearyl ester wax, hexadecylene aromatic alcohol, 2-octyldodecanol, benzyl alcohol and water.

In the abovementioned pharmaceutical formulations, the active compounds of general formula (I) should be present in a concentration of approximately from 0.1 to 99.5% by weight, preferably of approximately from 0.5 to 95% by weight of the total mixture.

The abovementioned pharmaceutical formulations may, in addition to the compounds of general formula (I), also comprise further pharmaceutically active compounds.

In general, it has been proved to be advantageous both in human and veterinary medicine to administer the active compound(s) in total amounts of from about 0.5 to 500, preferably from 1 to 100 mg/kg of body weight per 24 hours, if appropriate in the form of several individual doses, to obtain the desired results. An individual dose preferably contains the active compound(s) in amounts of from about 1 to 80, in particular from 1 to 30 mg/kg of body weight. However, it may be necessary to deviate from the specified dosages, depending on the nature and the body weight of the object to be treated, the nature and the severity of the disease, the formulation type and the administration of the medicament, and the time or interval within which administration is carried out.

Concrete Modes for Carrying Out the Invention

Following specific examples are preferred embodiments of the present invention, which should not be understood to form a restriction to the present invention in any way.

The present invention generally and/or specifically describes the materials and experimental methods used therein. Although many materials and operation methods used for carrying out the present invention are well known in the art, but the present invention still provide description in details as much as possible. Those skilled in the art clearly know that in the context, without particular explanations, the materials and operation methods used in the present invention would be those well known in the art.

The melting point of compounds was determined by RY-1 melting point apparatus, and the thermometer was not revised. The mass spectrum of compounds was determined by Micromass ZabSpec high resolution (a resolution of 1000). The $^1$H-NMR of compounds was determined by means of JNM-ECA-400 superconductive NMR instrument, operation frequency $^1$H-NMR 400 MHz, $^{13}$C-NMR 100 MHz.

EXAMPLES

Example 1 ethyl 2-(2,4,6-trifluorophenyl)-4-(2-chloro-4-fluorophenyl)-6-(chloromethyl)-1,4-dihydropyrimidine-5-carboxylate

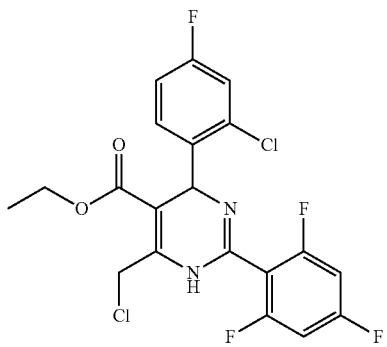 [SMILES: CCOC(=O)C1=C(CCl)NC(c2c(F)cc(F)cc2F)=NC1c1ccc(F)cc1Cl]

25 mmol of Ethyl 4-chloroacetate, 25 mmol of 2-chloro-4-fluorobenzaldehyde and 30 mmol of 2,4,6-trifluorobenzamidine acetate were dissolved in 100 ml of anhydrous ethanol, 0.6 ml of hydrogen chloride/ethanol was added, and the mixture was subjected to reflux for 72 h. The mixture was then evaporated to remove the solvents, ethyl acetate and water were added, and the phases were separated. The layer of ethyl acetate was dried over anhydrous sodium sulfate and subjected to a column chromatography to give 1.42 g of a white crystal and 1.77 g of ethyl 4-(2-chloro-4-fluorophenyl)-2-(2,4,6-trifluorophenyl)-6-hydroxyl-1,4-dihydropyrimidine-5-carboxylate. 1.77 g (4 mmol) of ethyl 4-(2-chloro-4-fluorophenyl)-2-(2,4,6-trifluorophenyl)-6-hydroxyl-1,4-dihydropyrimidine-5-carboxylate was dissolved in dichloromethane, 10 mmol of thionyl chloride was added, and the mixture was subjected to reflux for 8 h to give 19.6 g of ethyl 2-(2,4,6-trifluorophenyl)-4-2-chloro-4-fluorophenyl)-6-(chloromethyl)-1,4-dihydropyrimidine-5-carboxylate (yield 29.4%): $^1$H-NMR (400 MHz, DMSO-d6) δ 1.07(3H, t, J=7.0 Hz, CH$_3$); 4.76(2H, q, J=11.4 Hz, CH$_2$); 3.99(2H, q, J=7.0 Hz, CH$_2$); 6.02(1H, s, CH); 7.44-7.50(2H, m, ArH); 7.28-7.34(3H, m, ArH); 10.28(1H, br, NH). MS(FAB) 461.2 (M+).

Example 2 ethyl 2-(2,4,6-trifluorophenyl)-4-(2-chloro-4-fluorophenyl)-6-(tetrahydropyrrol-1-ylmethyl)-1,4-dihydropyrimidine-5-carboxylate

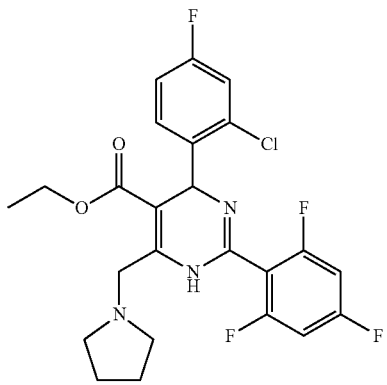 [SMILES: CCOC(=O)C1=C(CN2CCCC2)NC(c2c(F)cc(F)cc2F)=NC1c1ccc(F)cc1Cl]

300 mg of ethyl 4-(2-chloro-4-fluorophenyl)-2-(2,4,6-trifluorphenyl)-6-chloro-1,4-dihydropyrimidine-5-acetate, an intermediate, was dissolved in 10 ml of anhydrous DMF, a catalytic amount of KI and 0.1 g of K$_2$CO$_3$ were added, and then a mixture of 0.5 ml (0.43 g) of tetrahydropyrrole and 10 ml of anhydrous DMF was added dropwise under protection of N$_2$. The mixture was reacted at room temperature for 32 h under stirring, then filtrated under vacuum to remove insoluble substances, and extracted with 100 ml of water and 50 ml of ethyl acetate. The organic layer was washed with 50 ml of water for trice, and the aqueous layer was back-extracted with ethyl acetate. The organic layers were combined, then adjusted to be acidic with dilute hydrochloric acid, and extracted with 50 ml of water. The resulting aqueous layer was alkalified with NaHCO$_3$, extracted with ethyl acetate, dried over anhydrous NaSO$_4$, and dried by rotary evaporation to give 140 mg of a yellow solid (yield 43.5%): $^1$H-NMR (400 MHz, DMSO-d$_6$) δ 9.662(1H, br, NH), 7.418-7.278 (3H, m, ArH), 7.258-7.235 (2H, m, ArH), 6.000(1H, s, CH), 3.955-3.919 (2H, m, J=7.2 Hz, CH$_2$) 3.834 (2H, br, J=14.0 Hz, CH$_2$), 2.509-2.500(4H, m), 1.726 (4H, br), 1.065-1.030(3H, t, J=7.0 Hz, CH$_3$) MS (EI) M$^+$ 495.1.

Example 3 ethyl 2-(2,4,6-trifluorophenyl)-4-(2-chloro-4-fluorophenyl)-6-(hexahydropyridine-1-ylmethyl)-1,4-dihydropyrimidine-5-carboxylate

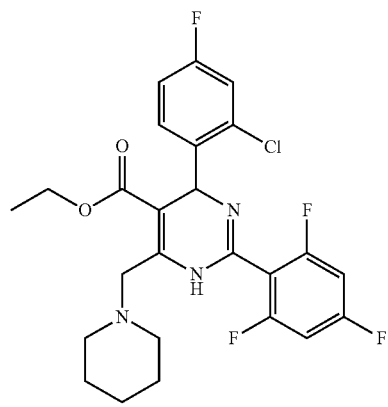 [SMILES: CCOC(=O)C1=C(CN2CCCCC2)NC(c2c(F)cc(F)cc2F)=NC1c1ccc(F)cc1Cl]

The method of Example 2 was used except that tetrahydropyrrole was replaced by hexahydropyridine to give 90 mg of a yellow solid (yield 27.2%): $^1$H-NMR (400 MHz, DMSO-d6)δ 9.490 (1H, br, NH), 7.275-7.272 (3H, m, ArH), 7.252-7.246 (2H, m, ArH), 6.007 (1H, s, CH), 3.958-3.922 (2H, q, J=7.3 Hz, CH$_2$), 3.758-3.601 (2H, dd, J=4.8 Hz, J=33.0 Hz, CH$_2$), 2.508-2.499 (4H, br), 1.524-1.397(4H, br), 1.397-1.385 (2H, br), 1.070-1.034 (3H, t, J=7.0 Hz, CH$_3$) MS(EI) M$^+$ 509.0.

Example 4 ethyl 2-(2,4,6-trifluorophenyl)-4-(2-chloro-4-fluorophenyl)-6-(4-methylpiperidin-1-ylmethyl)-1,4-dihydropyrimidine-5-carboxylate

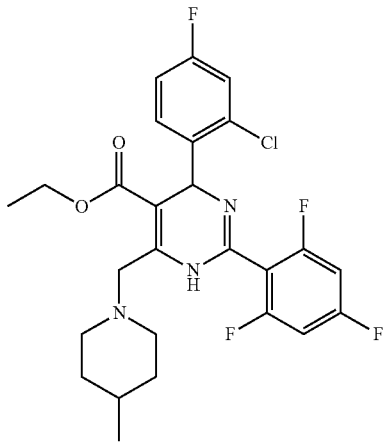 [SMILES: CCOC(=O)C1=C(CN2CCC(C)CC2)NC(c2c(F)cc(F)cc2F)=NC1c1ccc(F)cc1Cl]

The method of Example 2 was used except that tetrahydropyrrole was replaced by p-methylpiperidine to give 80 mg of a yellow solid (yield 23.5%): $^1$H-NMR (400 MHz, DMSO-d6) δ 9.486 (1H, br, NH), 7.475-7.424 (3H, m, ArH), 7.300-7.286 (2H, m, ArH), 6.007 (1H, s, CH), 4.036-3.963 (2H, q, J=7.2 Hz, CH$_2$), 3.740-3.660 (2H, dd, J=14.0 Hz, CH$_2$), 2.860-1.626 (4H, br), 1.340-1.192 (4H, br), 1.052-1.034 (3H, t, J=7.0 Hz, CH$_3$), 0.902-0.886 (4H, m) MS(EI) M$^+$ 523.1.

Example 5 ethyl 2-(2,4,6-trifluorophenyl)-4-(2-chloro-4-fluorophenyl)-6-(morpholin-1-ylmethyl)-1,4-dihydropyrimidine-5-carboxylate

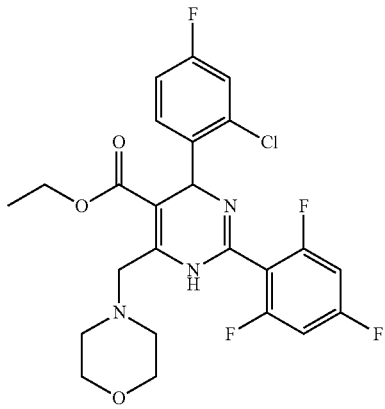 [SMILES: CCOC(=O)C1=C(CN2CCOCC2)NC(c2c(F)cc(F)cc2F)=NC1c1ccc(F)cc1Cl]

The method of Example 2 was used except that tetrahydropyrrole was replaced by morpholine to give 180 mg of a yellow solid (yield 54.5%): $^1$H-NMR (400 MHz, DMSO-d6) δ 9.629(1H, br, NH), 7.415-7.413 (2H, m, ArH), 7.278-7.259 (3H, m, ArH), 6.011 (1H, s, CH), 3.966-3.948 (2H, q, J=7.0 Hz, CH$_2$), 3.787-3.751 (2H, dd, J=14.01 Hz, CH$_2$), 3.614-3.608 (4H, br), 2.504 (4H, br), 1.056 (3H, t, J=7.0 Hz, CH$_3$) MS (EI) M$^+$ 511.1.

Example 6 ethyl 2-(2,4,6-trifluorophenyl)-4-(2-chloro-4-fluorophenyl)-6-(thiomorpholin-1-ylmethyl)-1,4-dihydropyrimidine-5-carboxylate

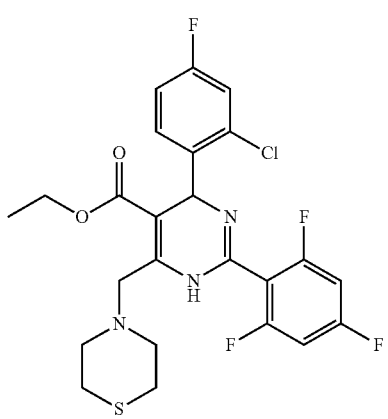 [SMILES: CCOC(=O)C1=C(CN2CCSCC2)NC(c2c(F)cc(F)cc2F)=NC1c1ccc(F)cc1Cl]

The method of Example 2 was used except that tetrahydropyrrole was replaced by thiomorpholine to give 280 mg of a yellow solid (yield 84.8%): $^1$H-NMR (400 MHz, DMSO-d6) δ 9.471 (1H, br, NH), 7.405 (2H, m, ArH), 7.242 (3H, m, ArH), 6.009 (1H, s, CH), 3.964-3.946 (2H, q, J=7.0 Hz, CH$_2$), 3.804-3.690 (2H, dd, J=14.01 Hz, CH$_2$), 2.716 (4H, br), 2.653 (4H, br), 1.053 (3H, t, J=7.0 Hz, CH$_3$) MS (EI) M$^+$ 527.0.

Example 7 ethyl 2-(2,4,6-trifluorophenyl)-4-(2-chloro-4-fluorophenyl)-6-(4-methylpiperazin-1-ylmethyl)-1,4-dihydropyrimidine-5-carboxylate

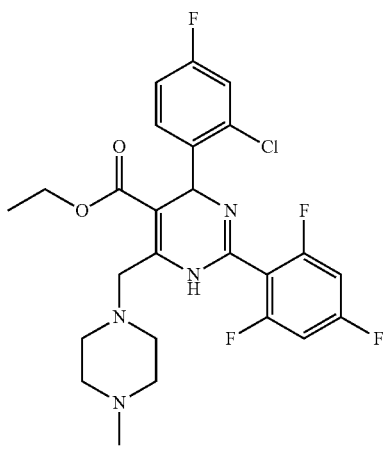 [SMILES: CCOC(=O)C1=C(CN2CCN(C)CC2)NC(c2c(F)cc(F)cc2F)=NC1c1ccc(F)cc1Cl]

The method of Example 2 was used except that tetrahydropyrrole was replaced by N-methylpiperazine to give 200 mg of a yellow solid (yield 60.6%): $^1$H-NMR (400 MHz, DMSO-d6) δ 9.523 (1H, br, NH), 7.410 (2H, m, ArH), 7.276 (3H, m, ArH), 6.008 (1H, s, CH), 3.963-3.945 (2H, q, J=7.0 Hz, CH$_2$), 3.740-3.628 (2H, dd, J=14.01 Hz, CH$_2$), 2.513-2.495 (8H, br), 2.155 (3H, s, CH$_3$), 1.056 (3H, t, J=7.0 Hz, CH$_3$) MS (EI) M$^+$ 524.2.

Example 8 ethyl 2-(2,4,6-trifluorophenyl)-4-(2-chloro-4-fluorophenyl)-6-(4-ethyl piperazin-1-ylmethyl)-1,4-dihydropyrimidine-5-carboxylate;

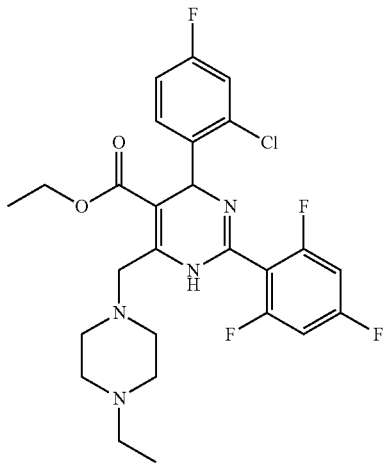 [SMILES: CCOC(=O)C1=C(CN2CCN(CC)CC2)NC(c2c(F)cc(F)cc2F)=NC1c1ccc(F)cc1Cl]

The method of Example 2 was used except that tetrahydropyrrole was replaced by N-ethylpiperazine to give 150 mg of a yellow solid (yield 42.9%): $^1$H-NMR (400 MHz, DMSO-d6) δ 9.488 (1H, br, NH), 7.263 (2H, m, ArH), 7.240 (3H, m, ArH), 6.011 (1H, s, CH), 3.965-3.948 (2H, q, J=7.0 Hz, CH$_2$), 3.733-3.667 (2H, dd, J=14.01 Hz, CH$_2$), 2.506-2.492 (10H, br), 1.057 (3H, t, J=7.0 Hz, CH$_3$), 0.984 (3H, t, J=7.2 Hz, CH$_3$) MS (EI) M$^+$ 538.0.

Example 9 ethyl 2-(2,4,6-trifluorophenyl)-4-(2-chloro-4-fluorophenyl)-6-(4-propyl piperazin-1-ylmethyl)-1,4-dihydropyrimidine-5-carboxylate

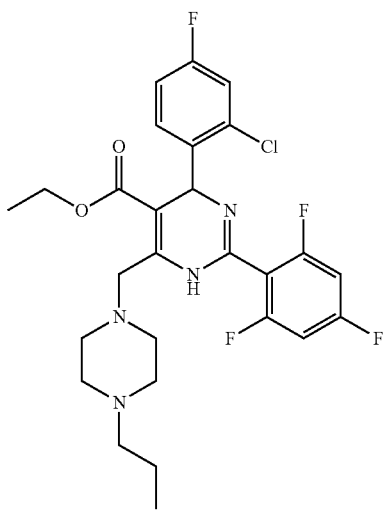 [SMILES: CCCN1CCN(CC2=C(C(=O)OCC)C(c3ccc(F)cc3Cl)N=C(c3c(F)cc(F)cc3F)N2)CC1]

The method of Example 2 was used except that tetrahydropyrrole was replaced by N-propylpiperazine to give 180 mg of a yellow solid (yield 50.0%): $^1$H-NMR (400 MHz, DMSO-d6) δ 9.489 (1H, br, NH), 7.263 (2H, m, ArH), 7.240 (3H, m, ArH), 6.008 (1H, s, CH), 3.964-3.946 (2H, q, J=7.0 Hz, CH$_2$), 3.731-3.663 (2H, dd, J=14.01 Hz, CH$_2$), 2.505-2.496 (8H, br), 2.214 (2H, t, J=7.5 Hz, CH$_2$), 1.447-1.392 (2H, q, J=7.5 Hz, CH$_2$), 1.057 (3H, t, J=7.0 Hz, CH$_3$), 0.843 (3H, t, J=7.2 Hz, CH$_3$) MS (EI) M$^+$ 552.0.

Example 10 ethyl 2-[2,4-difluoro-6-(tetrahydropyrrole-1-yl)phenyl]-4-(2-chloro-4-fluorophenyl)-6-(tetrahydropyrrole-1-ylmethyl)-1,4-dihydropyrimidine-5-carboxylate

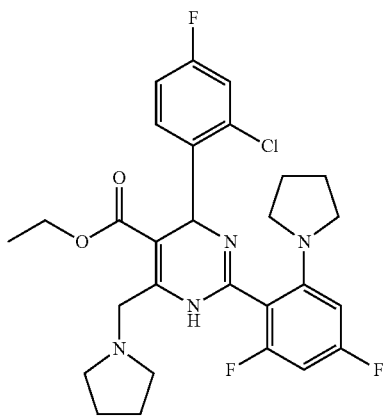 [SMILES: CCOC(=O)C1=C(CN2CCCC2)NC(c2c(F)cc(F)cc2N2CCCC2)=NC1c1ccc(F)cc1Cl]

650 mg (1.4 mmol) of ethyl 4-(2-chloro-4-fluorophenyl)-2-(2,4,6-trifluorophenyl)-6-chloro-1,4-dihydropyrimidine-5-acetate, an intermediate, was dissolved in 20 ml of anhydrous THF, a catalytic amount of KI and 0.35 ml of 90% (4.2 mmol) of tetrahydropyrrole were added, and the mixture was reacted under stirring at room temperature under protection of N$_2$, during which the solution was rapidly changed from yellow and transparent to reddish brown. After reacting under stirring for 28 h, the reaction was extracted with 30 ml of NaHCO$_3$ and 30 ml of ethyl acetate. The organic layer was washed with 30 ml of water for trice, and the aqueous layer was back-extracted with ethyl acetate. The organic layers were combined, washed with 30 ml of a saturated NaCl solution for trice, dried over anhydrous sodium sulfate, filtered, and recrystallized in a mixture of ethyl acetate and petroleum ether to give 10 mg of a plate crystal (yield 25.8%): $^1$H-NMR (400 MHz, DMSO-d6) δ 9.434 (1H, br, NH), 7.417-7.230 (3H, m, ArH), 6.364-6.243 (2H, m, ArH), 5.999 (1H, s, CH), 3.970-3.919 (2H, q, CH$_2$), 3.970-3.744 (d, 2H, J=14.0 Hz, CH$_2$), 3.149-2.965 (4H, br), 2.566-2.508 (4H, br), 1.718-1.687 (8H, br), 1.045 (3H, t, J=7.0 Hz, CH$_3$) MS M$^+$ 547.1.

Example 11 ethyl 2-[2,4-difluoro-6-(hexahydropyridin-1-yl)phenyl]-4-(2-chlor-4-fluorophenyl)-6-(hexahydropyridin-1-ylmethyl)-1,4-dihydropyrimidine-5-carboxylate

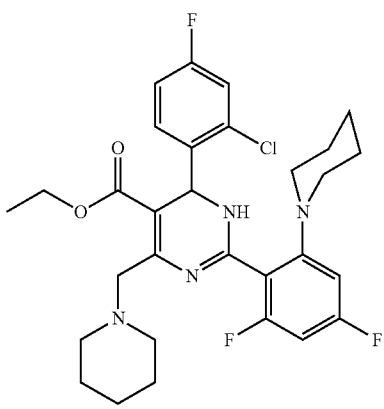 [SMILES: CCOC(=O)C1=C(CN2CCCCC2)N=C(c2c(F)cc(F)cc2N2CCCCC2)NC1c1ccc(F)cc1Cl]

520 mg (1.1 mmol) of ethyl 4-(2-chloro-4-fluorophenyl)-2-(2,4,6-trifluorophenyl)-6-chloro-1,4-dihydropyrimidine-5-acetate, an intermediate, was dissolved in 20 ml of anhydrous THF, a catalytic amount of KI and 0.3 ml (3.0 mmol) of hexahydropyridine were added, and the mixture was reacted at room temperature. After reacting under stirring for 40 h, the reaction was extracted with 30 ml of NaHCO₃ and 30 ml of ethyl acetate. The organic layer was washed with 30 ml of water for trice, and the aqueous layer was back-extracted with ethyl acetate. The organic layers were combined, washed with 30 ml of a saturated NaCl solution for trice, dried over anhydrous sodium sulfate, filtered, dried by rotary evaporation, and subjected to a column chromatography with ethyl acetate:petroleum ether=1:8 to give 360 mg of a yellow solid (yield 55.4%): $^1$H-NMR (400 MHz, DMSO-d6) δ 9.009(1H, br, NH), 7.419-7.213 (3H, m, ArH), 6.841-6.707 (2H, m, ArH), 6.008 (1H, s, CH), 3.967-3.915 (2H, q, J=7.0 Hz, CH$_2$), 3.826-3.654 (2H, dd, J=3.4 Hz, J=37.8 Hz, CH$_2$), 2.883-2.793 (4H, br), 2.510-2.496 (4H, br), 1.413-1.481 (12H, br), 1.040 (3H, t, J=7.0 Hz, CH$_3$) MS (EI) M$^+$ 574.1.

Example 12 ethyl 2-[2,4-difluoro-6-(4-methylpiperidine-1-yl)phenyl]-4-(2-chlor-4-fluorophenyl)-6-(4-methylpiperidine-1-ylmethyl)-1,4-dihydropyrimidine-5-carboxylate

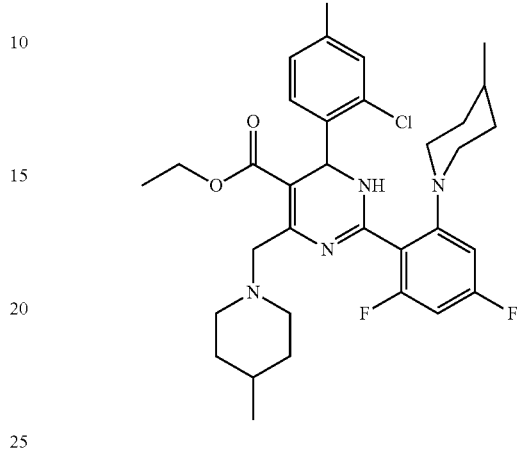

The method of Example 11 was used except that hexahydropyridine was replaced by 6-p-methylpiperidine to give 180 mg of a yellow solid (yield 46.2%): $^1$H-NMR (400 MHz, DMSO-d6) δ 9.001 (1H, br, NH), 7.426-7.351 (3H, m, ArH), 6.822-6.710 (2H, m, ArH), 5.999 (1H, s, CH), 3.935 (2H, q, J=7.2 Hz, CH$_2$) 3.688-3.783 (2H, dd J$_{1=}$=15.4 Hz J$_{2=}$=22.6 Hz, CH$_2$), 3.242-2.775 (4H, m), 2.564-2.496 (2H, m), 2.163-2.077(2H, m), 1.598-1.085 (8H, m), 1.057-1.039 (3H, t, J=7.0 Hz, CH$_3$) 0.912-0.846 (8H, m) MS (EI) M$^+$ 601.2.

Example 13 ethyl 2-[2,4-difluoro-6-(morpholin-1-yl)phenyl]-4-(2-chlor-4-fluorophenyl)-6-(morpholine-1-ylmethyl)-1,4-dihydropyrimidine-5-carboxylate

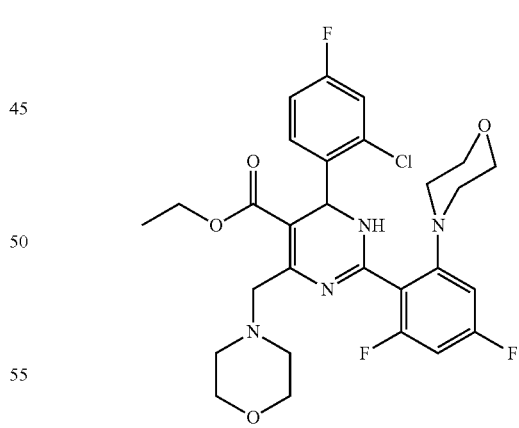

The method of Example 11 was used except that hexahydropyridine was replaced by morpholine to give 180 mg of a yellow, needle crystal (yield 28.1%): $^1$H-NMR (400 MHz, DMSO-d6) δ 9.254 (1H, br, NH), 7.444-7.320 (3H, m, ArH), 6.901-6.755 (2H, m, ArH), 5.993 (1H, s, CH), 3.957-3.940 (2H, q, J=7.0 Hz, CH$_2$) 3.771-3.755 (2H, dd J$_{1=}$=15.4 Hz J$_{2=}$=22.6 Hz, CH$_2$), 3.600 (4H, br), 3.402-3.333 (4H, m), 2.851-2.829 (4H, t, J=4.4 Hz), 2.508-2.499 (4H, m), 1.041 (3H, t, J=7.0 Hz, CH$_3$) MS (EI) M$^+$ 578.0.

Example 14 ethyl 2-[2,4-difluoro-6-(4-methylpiperazin-1-yl)phenyl]-4-(2-chlor-4-fluorophenyl)-6-(4-methylpiperazin-1-ylmethyl)-1,4-dihydropyrimidine-5-carboxylate

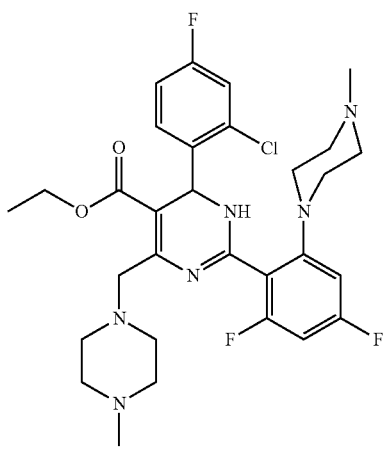 [SMILES: CCOC(=O)C1=C(CN2CCN(C)CC2)N=C(c2c(F)cc(F)cc2N2CCN(C)CC2)NC1c1ccc(F)cc1Cl]

The method of Example 11 was used except that hexahydropyridine was replaced by N-methylpiperidine to give 100 mg of a yellow solid (yield 12.7%): $^1$H-NMR (400 MHz, DMSO-d6) δ 9.082 (1H, br, NH), 7.441-7.340 (3H, m, ArH), 6.887-6.730 (2H, m, ArH), 5.991 (1H, s, CH), 3.958-3.922 (2H, q, J=7.0 Hz, CH$_2$), 3.815-3.720 (2H, dd J$_{1=}$=15.4 Hz J$_{2=}$=22.6 Hz, CH$_2$), 3.355 (4H, m), 2.851-2.840 (4H, m), 2.513-2.500 (4H, m), 2.357-2.056 (10H, m), 1.043 (3H, t, J=7.0 Hz, CH$_3$) MS (EI) M$^+$ 604.2.

Example 15 ethyl 2-(2,4,6-trifluorophenyl)-4-(2-chloro-4-fluorophenyl)-6-diethanolaminomethyl-1,4-dihydropyrimidine-5-carboxylate

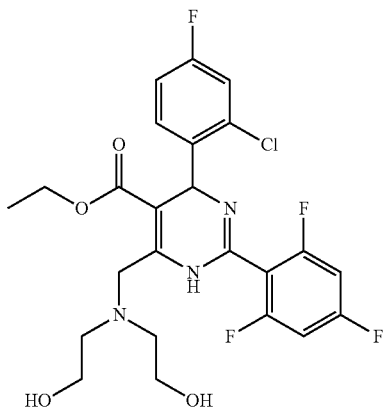 [SMILES: CCOC(=O)C1=C(CN(CCO)CCO)NC(c2c(F)cc(F)cc2F)=NC1c1ccc(F)cc1Cl]

The method of Example 2 was used except that tetrahydropyrrole was replaced by diethanolamine to give 230 mg of a white solid (yield 67.6%): $^1$H-NMR (400 MHz, DMSO-d6) δ 9.644 (1H, br, NH), 7.486-7.449 (1H, q, ArH), 7.396-7.367 (1H, dd, ArH), 7.251-7.220 (3H, m, ArH), 6.007 (1H, s, CH), 4.533-4.508 (2H, t, J=5.2 Hz, OH), 4.021-4.006 (2H, d, CH$_2$), 3.946-3.928 (2H, q, J=7.2 Hz, CH$_2$), 3.454-3.451 (4H, m, CH$_2$), 2.646-2.632 (4H, t, J=5.6 Hz, CH$_2$), 1.043 (3H, t, J=7.2 Hz, CH$_3$) MS(FAB)M$^+$530.0.

Example 16 ethyl 2-(2,4,6-trifluorophenyl)-4-(2-chloro-4-fluorophenyl)-6-(4-ethoxylacylpiperidine-1-ylmethyl)-1,4-dihydropyrimidine-5-carboxylate

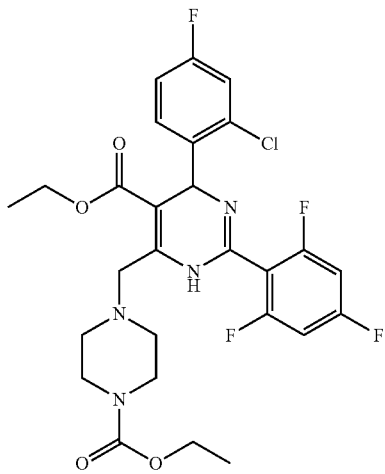 [SMILES: CCOC(=O)C1=C(CN2CCN(C(=O)OCC)CC2)NC(c2c(F)cc(F)cc2F)=NC1c1ccc(F)cc1Cl]

The method of Example 2 was used except that tetrahydropyrrole was replaced by N-ethoxylacylpiperazine to give 200 mg of a white solid (yield 52.6%): $^1$H-NMR (400 MHz, DMSO-d6) δ 9.581(1H, br, NH), 7.452-7.415 (1H, q, ArH), 7.408-7.379 (1H, dd, ArH), 7.280-7.215 (3H, m, ArH), 6.015 (1H, s, CH), 4.064-4.012 (2H, q, J=6.8 Hz, CH$_2$), 3.981-3.928 (2H, q, J=7.6 Hz, CH$_2$), 3.815-3.672 (2H, dd, CH$_2$), 3.400-3.391 (4H, t, CH$_2$), 2.506-2.447 (4H, t, CH$_2$), 1.181 (3H, t, J=6.8 Hz, CH$_3$), 1.050 (3H, t, J=7.6 Hz, CH$_3$) MS(FAB)M$^+$ 583.0.

Example 17 ethyl 2-(2,4,6-trifluorophenyl)-4-(2-chloro-4-fluorophenyl)-6-[(3-oxopiperazin-1-yl)methyl]-1,4-dihydropyrimidine-5-carboxylate

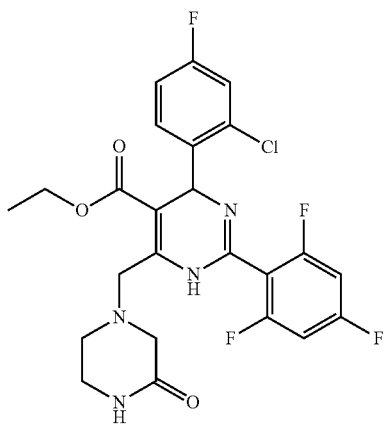 [SMILES: CCOC(=O)C1=C(CN2CCNC(=O)C2)NC(c2c(F)cc(F)cc2F)=NC1c1ccc(F)cc1Cl]

The method of Example 2 was used except that tetrahydropyrrole was replaced by ketopiperazine to give 110 mg of a yellow solid (yield 32.4%): $^1$H-NMR (400 MHz, DMSO-d6) δ 9.73 (1H, br, NH), 7.82 (1H, br, NH), 7.43-7.42 (2H, m, ArH), 7.29-7.25 (3H, m, ArH), 6.01 (1H, s, CH), 3.98-3.93

(2H, q, J=7.3 Hz, CH$_2$), 3.84-3.71 (2H, dd, CH$_2$), 3.18 (2H, m, CH$_2$), 3.06-3.05 (2H, q, CH$_2$), 2.51-2.50 (2H, m, CH$_3$), 1.050 (3H, t, J=7.3 Hz, CH$_3$) MS(FAB)M$^+$ 525.0.

Example 18 ethyl 2-(2,4,6-trifluorophenyl)-4-(2-chloro-4-fluorophenyl)-6-(morpholin-1-ylmethyl)-1,4-dihydropyrimidine-5-carboxylate hydrochloride

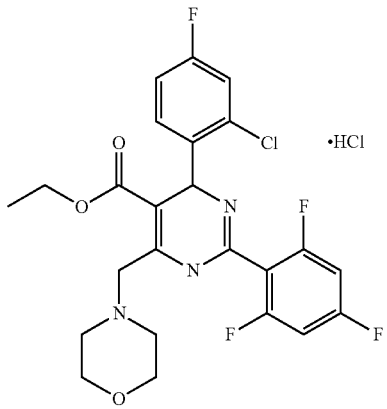 [SMILES: CCOC(=O)C1=C(CN2CCOCC2)NC(c2c(F)cc(F)cc2F)=NC1c1ccc(F)cc1Cl ; Cl]

0.18 g of the target compound obtained in Example 5 was dissolved in 2 ml of anhydrous ethanol, a solution of hydrogen chloride in ethyl-ether was added dropwise to precipitate a solid, and filtered to give 0.19 g of an off-white powdered solid. The solid was greatly soluble in water, soluble slightly in methanol and ethanol, and insoluble in dichloromethane, ethyl acetate, acetone, and the like.

Example 19

Determination of the Cytotoxicity and Antiviral Activity of the Present Compounds The cytotoxicity and antiviral activity of the compounds according to the present invention were determined by the methods described above, and the results were shown in Table 1.

TABLE 1

| Inhibitory effect of the present compounds on HBV DNA | | | |
| --- | --- | --- | --- |
| Example No. | IC$_{50}$(μM) | TC$_{50}$(μM) | SI |
| 8 | 6.7 | 41 | 6.16 |
| 13 | 4.4 | 55 | 12.72 |
| 15 | 6.7 | 54 | 8.11 |
| 18 | 2.4 | 31 | 13.37 |

What is claimed is:

1. A compound of general formula (I), or an optical isomer, pharmaceutically acceptable salt or hydrate thereof

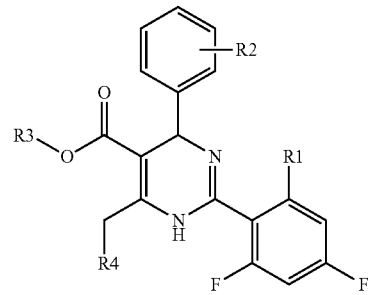

wherein:
R1 represents a halogen, a nitrogen-containing (C4-C14)-heterocyclic group, a (C1-C6)-alkylamino or a (C1-C6)-alkoxy, in which the nitrogen-containing heterocyclic group and alkyl moiety are optionally substituted by hydroxyl, a (C1-C6)-alkoxy, a (C1-C6)-alkoxycarbonyl, an aryl, a substituted aryl or a (C1-C6)-alkyl;
R2, for one or more occurrences, each represents a substituent selected from a halogen, nitro, hydroxyl, sulphonyl, a straight or branched (C1-C6)-alkyl, a (C1-C6)-alkoxyl, a (C1-C6)-alkoxycarbonyl, amino, a mono- or di-substituted amino, or an amido;
R3 represents a (C1-C6)-alkyl; and
R4 represents a halogen, a nitrogen-containing (C4-C8)-heterocyclic group, a (C1-C6)-alkylamino, a (C1-C6)-alkoxy, or a bi(C1-C6)-alkylamino, in which the nitrogen-containing heterocyclic group and alkyl moiety are optionally substituted by hydroxyl, a (C1-C6)-alkoxy, a (C1-C6)-alkoxycarbonyl, an aryl, a substituted aryl, oxo or a (C1-C6)-alkyl.

2. A compound of general formula (Ia), or an optical isomer, pharmaceutically acceptable salt or hydrate thereof,

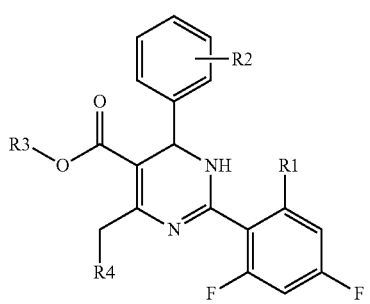

wherein:
R1 represents a halogen, a nitrogen-containing (C4-C14)-heterocyclic group, a (C1-C6)-alkylamino or a (C1-C6)-alkoxy, in which the nitrogen-containing heterocyclic group and alkyl moiety are optionally substituted by hydroxyl, a (C1-C6)-alkoxy, a (C1-C6)-alkoxycarbonyl, an aryl, a substituted aryl or a (C1-C6)-alkyl;
R2, for one or more occurrences, each represents a substituent selected from a halogen, nitro, hydroxyl, sulphonyl, a straight or branched (C1-C6)-alkyl, a (C1-C6)-alkoxyl, a (C1-C6)-alkoxycarbonyl, amino, a mono- or di-substituted amino, or an amido;
R3 represents a (C1-C6)-alkyl; and
R4 represents a halogen, a nitrogen-containing (C4-C8)-heterocyclic group, a (C1-C6)-alkylamino, a (C1-C6)- alkoxy, or a bi(C1-C6)-alkylamino, in which the nitrogen-containing heterocyclic group and alkyl moiety are optionally substituted by hydroxyl, a (C1-C6) -alkoxy, a (C1-C6)-alkoxycarbonyl, an aryl, a substituted aryl, oxo or a (C1-C6)-alkyl.

3. The compound according to claim 1 or 2, or an optical isomer, pharmaceutically acceptable salt or hydrate thereof, wherein
R1 represents a halogen, a nitrogen-containing (C4-C8)-heterocyclic group, a (C1-C4)-alkylamino or a (C1-C4)-alkoxy, in which the nitrogen-containing heterocyclic group and alkyl moiety are optionally substituted by hydroxyl, a (C1-C4)-alkoxy, a (C1-C4)-alkoxycarbonyl, an aryl, a substituted aryl or a (C1-C4)-alkyl;
R2, for one or more occurrences, each represents a substituent selected from a halogen, nitro, hydroxyl, sulphonyl straight or branched (C1-C4)-alkyl, a (C1-C4)-alkoxyl, a (C1-C4)-alkoxycarbonyl, amino, a mono- or di-substituted amino, or an amido;
R3 represents a (C1-C4)-alkyl; and
R4 represents a halogen, a nitrogen-containing (C4-C8)-heterocyclic group, a (C1-C4)-alkylamino, a (C1-C4)-alkoxy, or a bi(C1-C4)-alkylamino, in which the nitrogen-containing heterocyclic group and alkyl moiety are optionally substituted by hydroxyl, a (C1-C4)-alkoxy , a (C1-C4)-alkoxycarbonyl, an aryl, a substituted aryl, oxo or a (C1-C4)-alkyl.

4. The compound according to claim 1 or 2, or an optical isomer, pharmaceutically acceptable salt or hydrate thereof, wherein
R1 represents fluoro, tetrahydropyrrolyl, hexahydropyridyl, 4-methylpiperidyl, morpholinyl, thiomorpholinyl, 4-methyl piperazinyl, 4-ethylpiperazinyl, 4-propylpiperazinyl, diethanolamino, 4-ethoxylacylpiperazinyl, 3-oxopiperazinyl, methoxy or ethoxy;
R2, for one or more occurrences, each represents fluoro, chloro, bromo, iodo, hydroxyl, nitro, methyl, methoxy, amino or acetylamino;
R3 represents methyl, ethyl or propyl; and
R4 represents chloro, tetrahydropyrrolyl, hexahydropyridyl, 4-methylpiperidyl, morpholinyl, thiomorpholinyl, 4-methyl piperazinyl, 4-ethylpiperazinyl, 4-propylpiperazinyl, diethanolamino, 4-ethoxylacylpiperazinyl or 3-oxopiperazinyl.

5. The compound according to claim 1 or 2, or an optical isomer, pharmaceutically acceptable salt or hydrate thereof, which compound is selected from:
(1) ethyl 2-(2,4,6-trifluorophenyl)-4-(2-chloro-4-fluorophenyl)-6-(chloromethyl)-b 1,4-dihydropyrimidine-5-carboxylate;
(2) ethyl 2-(2,4,6-trifluorophenyl)-4-(2-chloro-4-fluorophenyl)-6-(tetrahydropyrrol-1-ylmethyl)-1,4-dihydropyrimidine-5-carboxylate;
(3) ethyl 2-(2,4,6-trifluorophenyl)-4-(2-chloro-4-fluorophenyl)-6-(hexahydropyridin-1-ylmethyl)-1,4-dihydropyrimidine-5-carboxylate;
(4) ethyl 2-(2,4,6-trifluorophenyl)-4-(2-chloro-4-fluorophenyl)-6- (4-methylpiperidin-1-ylmethyl)-1,4-dihydropyrimidine-5-carboxylate;
(5) ethyl 2-(2,4,6-trifluorophenyl)-4-(2-chloro-4-fluorophenyl)-6- (morpholin-1-ylmethyl)-1,4-dihydropyrimidine-5-carboxylate;
(6) ethyl 2-(2,4,6-trifluorophenyl)-4-(2-chloro-4-fluorophenyl)-6- (thiomorpholin-l-ylmethyl) -1,4-dihydropyrimidine-5-carboxylate;
(7) ethyl 2-(2,4,6-trifluorophenyl)-4-(2-chloro-4-fluorophenyl)-6-(4-methyl piperazin-1-ylmethyl)-1,4-dihydropyrimidine-5-carboxylate;
(8) ethyl 2-(2,4,6-trifluorophenyl)-4-(2-chloro-4-fluorophenyl)-6-(4-ethyl piperazin-1-ylmethyl)-1,4-dihydropyrimidine-5-carboxylate;
(9) ethyl 2-(2,4,6-trifluorophenyl)-4-(2-chloro-4-fluorophenyl)-6-(4-propyl piperazin-1-ylmethyl)-1,4-dihydropyrimidine-5-carboxylate;
(10) ethyl 2-[2,4-difluoro-6-(tetrahydropyrrol-1-yl)phenyl]-4-(2-chloro- 4-fluorophenyl)-6-(tetrahydropyrrol-1-ylmethyl)-1,4-dihydropyrimidine-5-carboxylate;
(11) ethyl 2-[2,4-difluoro-6-(hexahydropyridin-1-yl)phenyl]-4-(2-chlor- 4fluorophenyl)-6-(hexahydropyridin-1-ylmethyl)-1,4-dihydropyrimidine-5-carboxylate;
(12) ethyl 2[2,4-difluoro-6-(4-methylpiperidin-1-yl)phenyl]-4-(2-chlor-4fluorophenyl)-6-(4-methylpiperidin-1-ylmethyl)-1,4-dihydropyrimidine-5-carboxylate;
(13) ethyl 2-[2,4-difluoro-6-(morpholin-1-yl)phenyl]-4-(2-chlor-4fluorophenyl)-6-(morpholin-1-ylmethyl)-1,4-dihydropyrimidine-5-carboxylate;
(14) ethyl 2-[2,4-difluoro-6-(4-methylpiperazin-1-yl)phenyl]-4-(2-chlor- 4fluorophenyl)-6-(4-methylpiperazin-1-ylmethyl)-1,4-dihydropyrimidine-5-carboxylate;
(15) ethyl 2-(2,4,6-trifluorophenyl)-4-(2-chloro-4-fluorophenyl)-6diethanolaminomethyl-1,4-dihydropyrimidine-5-carboxylate;
(16) ethyl 2-(2,4,6-trifluorophenyl)-4-(2-chloro-4-fluorophenyl)-6-(4ethoxylacylpiperazin-1-ylmethyl)-1,4-dihydropyrimidine-5-carboxylate;
(17) ethyl 2-(2,4,6-trifluorophenyl)-4-(2-chloro-4-fluorophenyl)-6-[(3-oxopiperazin-1-yl)methyl]-1,4-dihydropyrimidine-5-carboxylate; and
(18) ethyl 2-(2,4,6-trifluorophenyl)-4-(2-chloro-4-fluorophenyl)-6- (morpholin-1-ylmethyl)-1,4-dihydropyrimidine-5-carboxylate hydrochloride.

6. A pharmaceutical composition comprising a therapeutically effective amount of the compound according to claim 1 or 2, optionally pharmaceutically acceptable carriers, and optionally other pharmaceutically active compounds.

7. A method of treating an acute or chronic infection caused by hepatitis B viruses, comprising administering a subject in need thereof a therapeutically effective amount of the compound according to claim 1 or 2.

* * * * *